(12) United States Patent
Maki et al.

(10) Patent No.: US 8,622,933 B2
(45) Date of Patent: Jan. 7, 2014

(54) MEDICAL GUIDEWIRE

(75) Inventors: Hideaki Maki, Aichi (JP); Shinichi Goto, Aichi (JP); Tadakazu Kato, Aichi (JP)

(73) Assignee: Asahi Intecc Co., Ltd., Aichi (JP)

( * ) Notice: Subject to any disclaimer, the term of this patent is extended or adjusted under 35 U.S.C. 154(b) by 91 days.

(21) Appl. No.: 12/976,273

(22) Filed: Dec. 22, 2010

(65) Prior Publication Data

US 2011/0178436 A1 Jul. 21, 2011

(30) Foreign Application Priority Data

Jan. 21, 2010 (JP) ................................ 2010-010576

(51) Int. Cl.
*A61B 5/00* (2006.01)

(52) U.S. Cl.
USPC ........................................................ 600/585

(58) Field of Classification Search
USPC ......... 600/433–434, 585; 604/164.01, 164.13
See application file for complete search history.

(56) References Cited

U.S. PATENT DOCUMENTS

| | | | |
|---|---|---|---|
| 4,832,047 A * | 5/1989 | Sepetka et al. | 600/585 |
| 5,213,111 A * | 5/1993 | Cook et al. | 600/585 |
| 5,840,046 A | 11/1998 | Deem | |
| 5,876,356 A * | 3/1999 | Viera et al. | 600/585 |
| 5,984,878 A | 11/1999 | Engelson | |
| 6,042,876 A | 3/2000 | Deem | |
| 6,494,847 B1 * | 12/2002 | Richardson et al. | 600/585 |
| 2003/0100848 A1 * | 5/2003 | Gosiengfiao et al. | 600/585 |
| 2004/0167436 A1 * | 8/2004 | Reynolds et al. | 600/585 |
| 2006/0041204 A1 | 2/2006 | Kato | |
| 2007/0293791 A1 * | 12/2007 | Lee et al. | 600/585 |
| 2008/0004546 A1 | 1/2008 | Kato | |
| 2008/0281230 A1 * | 11/2008 | Kinoshita et al. | 600/585 |

FOREIGN PATENT DOCUMENTS

| | | |
|---|---|---|
| EP | 0769306 A2 | 4/1997 |
| EP | 1875941 A1 | 1/2008 |
| JP | 2005278795 A | 10/2005 |
| JP | 2007-075531 A | 3/2007 |
| JP | 200812276 A | 1/2008 |
| JP | 2008237621 A | 10/2008 |
| JP | 2008307367 A | 12/2008 |
| WO | 9748330 A1 | 12/1997 |
| WO | 2009119387 A1 | 10/2009 |

OTHER PUBLICATIONS

European Search Report for EP 10197078, dated Apr. 18, 2011.
Office Action for JP 2010-010576 mailed Dec. 15, 2011.
A Chinese Office Action dated Jul. 20, 2012 in Chinese Application No. 201110025798.1.

(Continued)

*Primary Examiner* — Max Hindenburg
*Assistant Examiner* — Jonathan M Foreman
(74) *Attorney, Agent, or Firm* — Lowe Hauptman & Ham, LLP

(57) ABSTRACT

There is provided a medical guidewire which reduces the resistance with a curved guiding catheter, and has improved durability that can keep the resistance reduced for a long time. A core shaft of the medical guidewire has a second cylindrical part, with a smaller diameter than that of a coiled body, on a proximal end side of the coiled body. This second cylindrical part is coated with a hydrophilic material. Further, the hydrophilic material coated on the second cylindrical part has a larger thickness than a hydrophilic material coated on the coiled body.

19 Claims, 8 Drawing Sheets

(56) References Cited

OTHER PUBLICATIONS

A Japanese Office Action dated Jun. 12, 2012 in JP Application No. 2010-010576.

A Chinese Office Action dated Jul. 8, 2013 in Chinese Application No. 201110025798.1.

A Second Office Action in Chinese Application No. 201110025798.1, Dec. 18, 2012.

* cited by examiner

MEDICAL GUIDEWIRE

CROSS REFERENCE TO RELATED APPLICATIONS

This application is based on Japanese Patent Application No. 2010-010576 filed with the Japan Patent Office on Jan. 21, 2010, the entire content of which is hereby incorporated by reference.

TECHNICAL FIELD

The present invention relates to a medical guidewire.

BACKGROUND ART

There have conventionally been proposed a variety of medical guidewires for guiding a medical equipment such as a catheter which is used by being inserted into tubular organs such as blood vessels, digestive tracts and ureters, and intracorporeal tissues.

For example, a medical guidewire described in Patent Literature 1 (Japanese Patent Application Laid-Open No. 2008-307367) is made up of a wire body, a coil, a resin coating layer coated on this coil, and an annular member. The wire body has a certain diameter in a portion closer to the rear end than a tip portion, which is formed in tapered shape. The coil is a spiral coil that is wound around the tip portion of the wire body. The annular member is filled in a stepped space between a proximal end portion of the resin coating layer and the wire body.

Further, a hydrophilic lubricating layer is formed on the outer surface of the resin coating layer and the outer surface of the annular member in the medical guidewire described in Patent Literature 1.

It is described in Patent Literature 1 that in the case of using the medical guidewire and medical equipment in combination, the medical guidewire is prevented from getting caught in the medical equipment according to the invention described in this literature.

SUMMARY OF INVENTION

In the medical guidewire described in Patent Literature 1, the outer surface of the resin coating layer and the outer surface of the annular member are coated with the hydrophilic lubricating layer. However, there has been a problem with this medical guidewire in that in a curved area of a guiding catheter, the sliding resistance between the medical guidewire and the guiding catheter increases.

Further, during an operation by a physician, the medical guidewire and the guiding catheter continuously slide. It has thus been necessary to consider the durability of the medical guidewire which can keep the sliding resistance between the medical guidewire and the guiding catheter reduced as long as possible.

Moreover, in the medical guidewire described in Patent Literature 1, the annular member is filled in the stepped space between the proximal end portion of the resin coating layer and the wire body. However, a depressed portion with a corner is formed between the wire body and the annular member. There has thus been a problem in that the resistance generated at the time of manipulating the medical guidewire also increases due to this depressed portion.

Furthermore, since the depressed portion of the medical guidewire described in Patent Literature 1 has the corner, there has been a problem in that blood or bodily fluid may be accumulated in this depressed portion.

The present invention has been made in view of such circumstances. A first object of the present invention is to provide a medical guidewire reduced in resistance generated in the case of curving a guiding catheter. Further, a second object of the present invention is to provide a medical guidewire improved in durability that can keep the resistance reduced for a long time. Moreover, a third object of the present invention is to provide a medical guidewire which does not inhibit the flow of blood or bodily fluid at the time of manipulation.

A medical guidewire of the present invention is a medical guidewire including a core shaft and a coiled body that covers at least a tip portion of the core shaft, wherein especially the core shaft has a cylindrical part, with a smaller diameter than that of the coiled body, on a proximal end side of the coiled body, and the cylindrical part is coated with a hydrophilic material.

BRIEF DESCRIPTION OF DRAWINGS

The foregoing and other objects, features, aspects and advantages of the invention will become more apparent from the following detailed description when taken in conjunction with the accompanying drawings.

DESCRIPTION OF EMBODIMENTS

Figure 1:
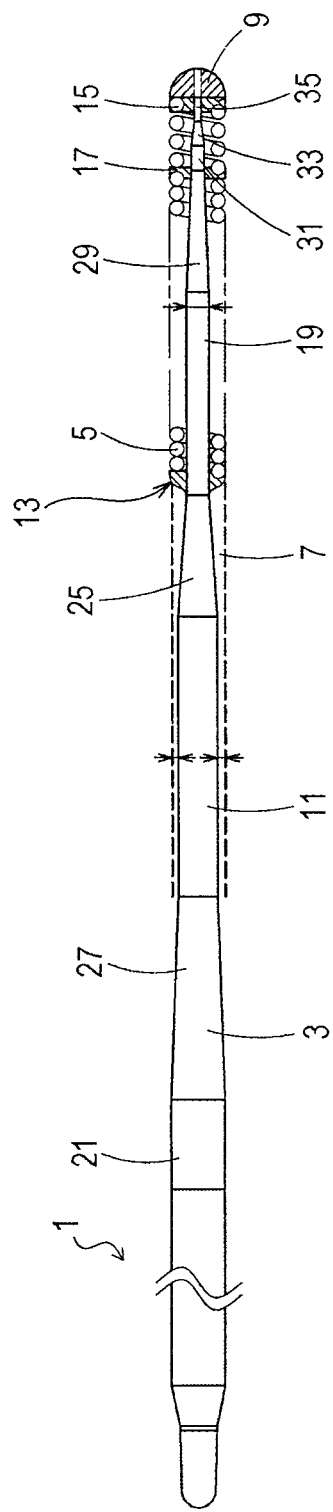
FIG. 1 illustrates an overall view of a medical guidewire according to a first embodiment of the present invention.

A first aspect of the invention is a medical guidewire including a core shaft and a coiled body that covers at least a tip portion of the core shaft, wherein especially the core shaft has a cylindrical part, with a smaller diameter than that of the coiled body, on a proximal end side of the coiled body, and the cylindrical part is coated with a hydrophilic material.

Further, a second aspect of the invention is the medical guidewire according to the first aspect, wherein the coiled body is also coated with the hydrophilic material, and a thickness of the hydrophilic material coated on the cylindrical part is larger than that of the hydrophilic material coated on the coiled body.

Further, a third aspect of the invention is the medical guidewire according to the second aspect, wherein a diameter of the cylindrical part including the hydrophilic material is smaller than that of the coiled body including the hydrophilic material.

Further, a fourth aspect of the invention is the medical guidewire according to any one of the first to third aspects, wherein an area from a proximal end portion of the coiled body to the cylindrical part is formed in streamlined shape.

Further, a fifth aspect of the invention is the medical guidewire according to the fourth aspect, wherein a middle area from the proximal end portion of the coiled body to the cylindrical part is formed in linear shape.

Further, a sixth aspect of the invention is the medical guidewire according to any one of the first to fifth aspects, wherein the cylindrical part is provided within a range of 50 to 350 mm from the tip of the core shaft.

According to the first aspect of the invention, the core shaft of the medical guidewire has the cylindrical part, with a smaller diameter than that of the coiled body, on the proximal end side of the coiled body. Further, the cylindrical part is coated with the hydrophilic material. It is thus possible to ensure a space between the guiding catheter and the cylindrical part of the medical guidewire inserted inside the guiding catheter. Moreover, this core shaft is provided with the cylindrical part having a certain diameter. Therefore, even in the case of the inner surface of the guiding catheter and the outer surface of the guidewire coming into contact with each other when the guiding catheter is curved, the manipulability of the guidewire remains unchanged. Furthermore, the cylindrical part is coated with the hydrophilic material. It is thus possible to further reduce the sliding resistance between the guiding catheter and the medical guidewire. Hence it is possible to provide a medical guidewire with favorable manipulability for a physician who performs an operation.

Further, according to the second aspect of the invention, the coiled body is also coated with the hydrophilic material, and the thickness of the hydrophilic material coated on the cylindrical part is larger than that of the hydrophilic material coated on the coiled body. Therefore, in addition to the effect of the first aspect, even in the case of the physician continuing the operation for a long period of time, it is possible to keep the resistance between the guiding catheter and the medical guidewire reduced. That is, the durability of the medical guidewire can be improved.

Further, according to the third aspect of the invention, the diameter of the cylindrical part including the hydrophilic material is smaller than that of the coiled body including the hydrophilic material. Therefore, in addition to the effect of the second aspect, it is possible to provide a medical guidewire with further favorable manipulability for the physician who performs the operation.

Further, according to the fourth aspect of the invention, the area from the proximal end portion of the coiled body to the cylindrical part is formed in streamlined shape. Therefore, in addition to the effect of the first aspect, the sliding resistance can be reduced in the case of pulling the medical guidewire inside the catheter, a tubular organ or an intracorporeal tissue. Hence it is possible to provide a medical guidewire with further favorable manipulability for the physician who performs the operation.

According to the fifth aspect of the invention, the middle area from the proximal end portion of the coiled body to the cylindrical part is formed in linear shape. Therefore, in addition to the effect of the fourth aspect, the blood or the bodily fluid is not accumulated, and the flow of the blood or the bodily fluid is not inhibited.

Further, according to the invention in accordance with the sixth aspect of the invention, the cylindrical part is provided within the range of 50 to 350 mm from the tip of the core shaft. It is thus possible to provide the medical guidewire particularly suitable for a curved shape that occurs in the case of applying the guiding catheter to the heart.

Hereinafter, the medical guidewire of the present invention will be described based on preferred embodiments illustrated in the drawings.

First Embodiment

FIG. 1 illustrates an overall view of a medical guidewire according to a first embodiment of the present invention.

It is to be noted that in FIG. 1, a description is given with the left side defined as a "proximal end", and the right side defined as a "tip" for convenience of description.

Further, in FIG. 1, the medical guidewire is reduced in length direction, and illustrated in an overall schematic manner for the sake of easy understanding. An overall size illustrated in FIG. 1 is thus different from an actual size.

In FIG. 1, a medical guidewire 1 is made up of a core shaft 3 and a coiled body 5 that covers a tip portion of the core shaft 3. The tip portion of the core shaft 3 and a tip portion of the coiled body 5 are fixed to each other at an extreme tip portion 9.

A material for the core shaft 3 is not particularly limited. In the present embodiment, stainless steel (SUS304) is used as the material for the core shaft 3. Other than that, a material such as a super elastic alloy like an Ni—Ti alloy, a piano wire, or a tungsten wire may be used.

As a whole, the core shaft 3 has a shape tapering down from the proximal end side toward the tip side. The core shaft 3 includes: a first cylindrical part 21 located in a position with a predetermined distance from the proximal end; a first taper part 27 adjacent to the tip side of the first cylindrical part 21; a second cylindrical part 11 (corresponding to the cylindrical part of the present invention) adjacent to the tip side of the first taper part 27; a second taper part 25 adjacent to the tip side of the second cylindrical part 11; a third cylindrical part 19 adjacent to the tip side of the second taper part 25; a third taper part 29 adjacent to the tip side of the third cylindrical part 19; a fourth cylindrical part 31 adjacent to the tip side of the third taper part 29; a taper press part 33 adjacent to the tip side of the fourth cylindrical part 31; and a cylindrical press part 35 adjacent to the tip side of the taper press part 33.

It is to be noted that the taper press part 33 is one with its side section formed in taper shape by pressing. The cylindrical press part 35 is one with its side section formed in cylindrical shape by pressing.

The second cylindrical part 11 is formed in a range of 50 to 350 mm from the tip of the medical guidewire 1. Herein, the range of 50 to 350 mm is a range corresponding to an area where the medical guidewire 1 is curved by a relatively large amount when used along with a guiding catheter disposed in an area from a femoral artery to a heart.

Herein, an operation of using the medical guidewire 1 and the guiding catheter as medical equipment in combination will be described with reference to the drawings.

Figure 6:
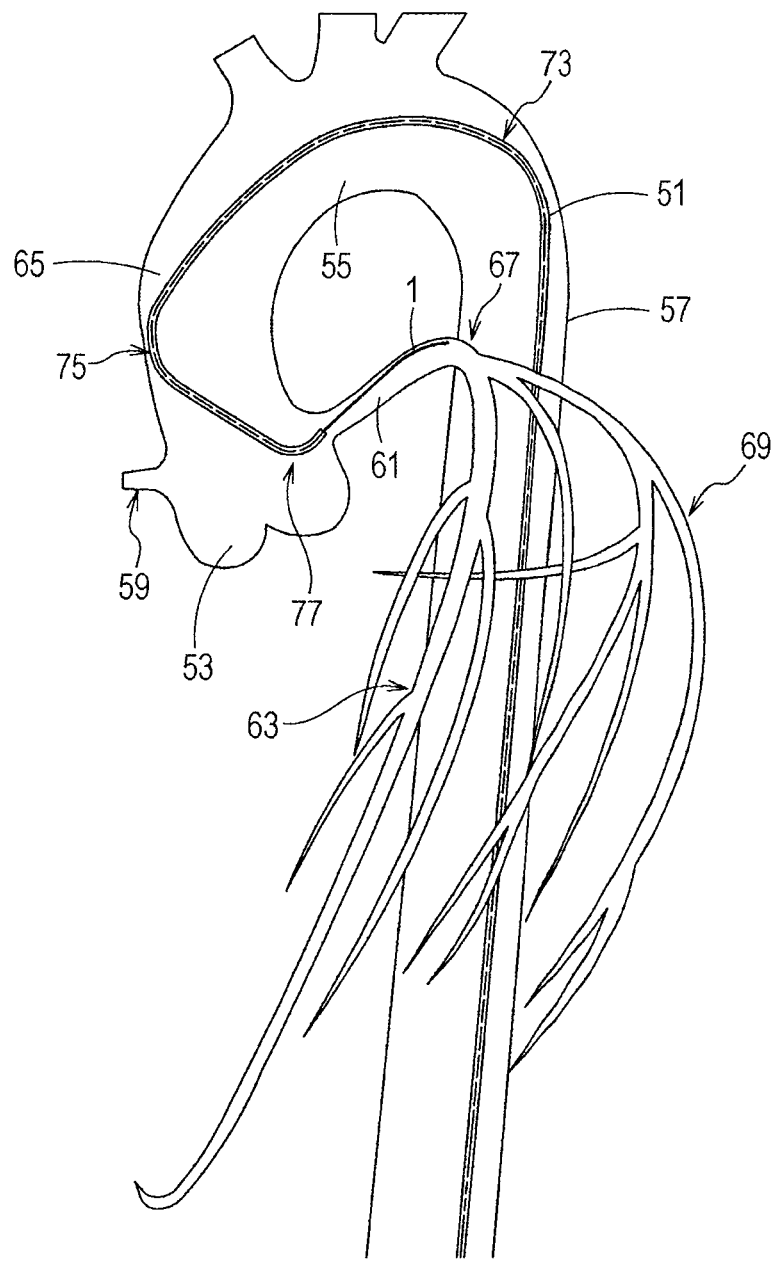
FIG. 6 illustrates a view of the state of a guiding catheter disposed in an area from a femoral artery to a heart, and a medical guidewire with its tip having reached a left main trunk of a left coronary artery.
Figure 7:
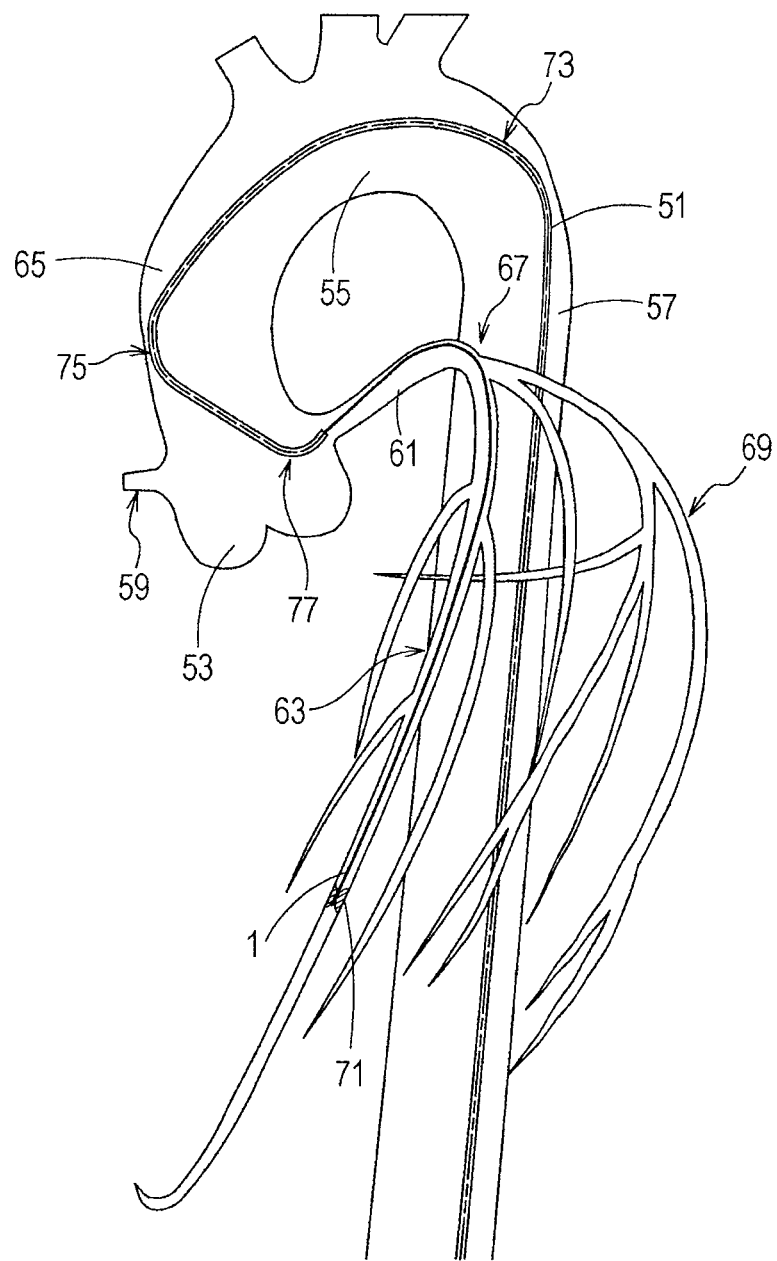
FIG. 7 illustrates a view of the state of the guiding catheter disposed in the area from the femoral artery to the heart and the medical guidewire with its tip having reached a stenosis part located in a left anterior descending artery of the left coronary artery.
Figure 8:
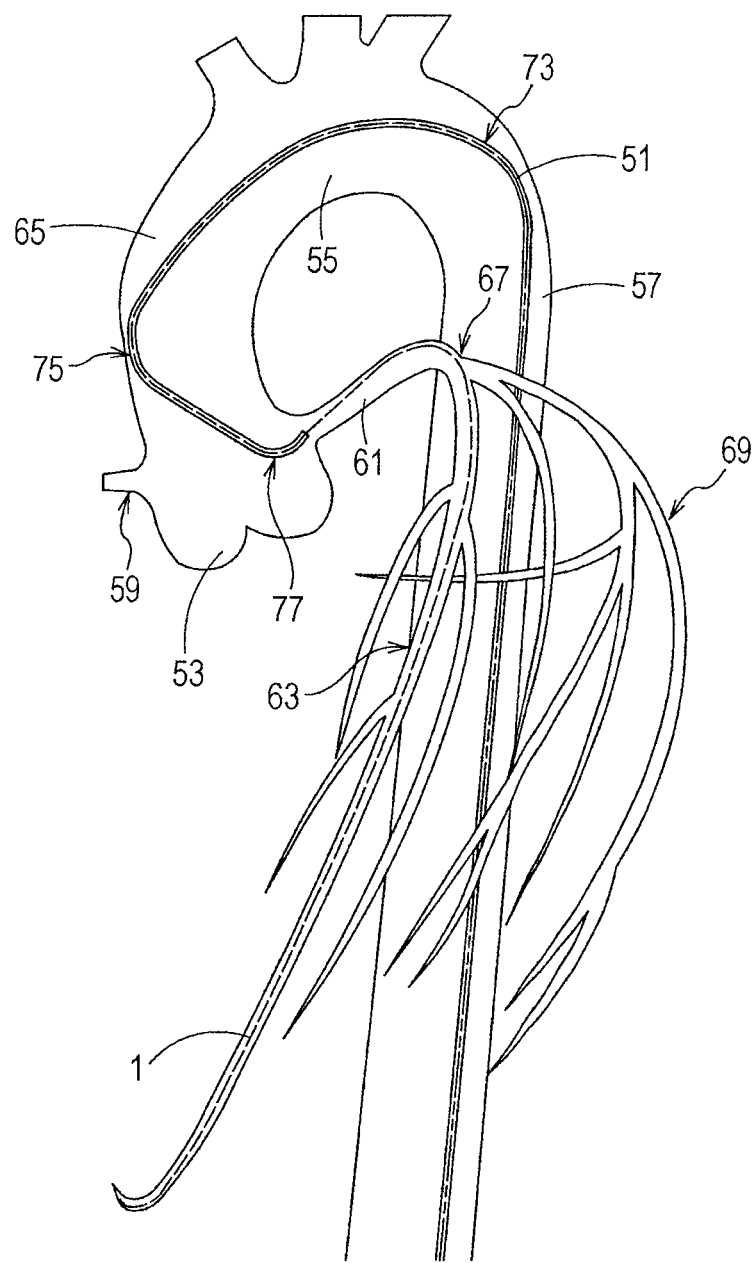
FIG. 8 illustrates a view of the state of the guiding catheter disposed in the area from the femoral artery to the heart and the medical guidewire with its tip having reached a distal part of the left anterior descending artery.

FIGS. 6 to 8 each illustrate an explanatory drawing of the state of a guiding catheter 51 as medical equipment disposed in the area from the femoral artery to the heart, and the medical guidewire 1. FIG. 6 illustrates a state where the tip of the medical guidewire 1 has reached a left main trunk 61 of a left coronary artery 67. FIG. 7 illustrates a state where the tip of the medical guidewire 1 has reached a stenosis part 71 located in a left anterior descending artery 63 of the left coronary artery 67. FIG. 8 illustrates a state where the tip of the medical guidewire 1 has reached a distal part of the left anterior descending artery 63.

In this operation, first, as illustrated in FIG. 6, a tip portion of the guiding catheter 51 is made to proceed from the femoral artery to a descending aorta 57, an aortic arc 55 and an ascending aorta 65. This tip portion is then fixedly placed in a right coronary artery 59 just before an aortic valve 53 or at one inlet of the left coronary artery 67 (in FIG. 6, the guiding catheter 51 is fixedly placed at the inlet of the left coronary artery 67). The medical guidewire 1 is then inserted inside the fixedly placed guiding catheter 51, and protruded from the tip portion of the guiding catheter 51.

It is to be noted that the left coronary artery 67 is made up of the left main trunk 61, a left circumflex artery 69 and the left anterior descending artery 63. The left main trunk 61 is located upstream of the artery. The left circumflex artery 69 is located downstream of one branch in the left main trunk 61. The left anterior descending artery 63 is located downstream of the other branch in the left main trunk 61.

Herein, for example, in the case where the stenosis part 71 exists in a predetermined position of the left anterior descending artery 63, as illustrated in FIG. 7, the medical guidewire 1 is made to proceed to the position of the stenosis part 71. Thereby, the portion formed with the stenosis part 71 in the artery is treated.

Further, as illustrated in FIG. 8, the guidewire 1 can also be made to proceed to the distal part of the left anterior descending artery 63.

As illustrated in FIGS. 6 to 8, the fixedly placed guiding catheter 51 extends almost linearly from the femoral artery, and is curved in a first area 73 from the descending aorta 57 to the aortic arc 55. Moreover, the guiding catheter 51 is curved in a second area 75 from the ascending aorta 65 to the left coronary artery 67, with a smaller radius of curvature, and is curved in a third area 77 in the vicinity of the inlet of the left coronary artery 67, with an even smaller radius of curvature.

As described above, the second cylindrical part 11 is formed in the range of 50 to 350 mm from the tip of the medical guidewire 1. This range corresponds to the third area 77, the second area 75, and the first area 73.

In such a manner, in the medical guidewire 1, the range of 50 to 350 mm from the tip is formed in cylindrical shape as the second cylindrical part 11. This is for making uniform the sliding resistance between the guiding catheter 51 and the medical guidewire 1 in the third area 77, the second area 75 and the first area 73.

In contrast, when the second cylindrical part 11 is formed not in cylindrical shape but in, for example, tapered shape or conical shape, the sliding resistance may change in the third area 77, the second area 75 or the first area 73. Hence the manipulability of the medical guidewire 1 may decrease during an operation.

Further, the radii of curvature of the medical guidewire 1 in the second area 75 and the third area 77 are smaller than the radius of curvature in the first area 73.

Hence, the effect can also be obtained even when the formation range of the second cylindrical part 11 is restricted only to a range corresponding to the second area 75 and the third area 77. In that case, the second cylindrical part 11 may be formed in a range of 50 to 250 mm from the tip of the medical guidewire 1.

It is to be noted that in the present embodiment, the second cylindrical part 11 of the medical guidewire 1 is formed based on the shape of the guiding catheter 51 disposed in the area from the femoral artery to the heart. However, a curved position varies depending on the site in the body where the guiding catheter 51 is used. Therefore, in the case of using the guiding catheter 51 in another site in the body, the second cylindrical part 11 of the medical guidewire 1 is preferably formed in accordance with a curved position of that site in the body.

Moreover, in the case of using the medical guidewire 1 and a medical equipment other than the guiding catheter in combination, the second cylindrical part 11 is preferably formed in accordance with a curved shape of the medical equipment.

However, in any case, common points are to form the second cylindrical part 11 in cylindrical shape, to form the second cylindrical part 11 on the side closer to the proximal end than the coiled body 5, and to form the second cylindrical part 11 with a smaller outer diameter than that of the coiled body 5.

Forming the second cylindrical part 11 on the proximal end side of the coiled body 5, with the smaller outer diameter than that of the coiled body 5, exerts the following effect.

That is, when the coiled body 5 including the extreme tip portion 9 of the medical guidewire 1 is inserted inside the body, the coiled body 5 passes through the inside of the body. Hence, in the body, a cavity corresponding to the outer diameter of the coiled body 5 is formed on the proximal end side of the coiled body 5. The second cylindrical part 11 is formed, with a smaller outer diameter than that of the coiled body 5, on the proximal end side of the coiled body 5. For this reason, a space is generated between the second cylindrical part 11 and an inner wall of the cavity formed by passage of the coiled body 5.

Generation of this space can reduce the sliding resistance between the second cylindrical part 11 and the inner wall of the cavity.

Further, as illustrated using FIGS. 6 to 8, when the guiding catheter 51 is curved, or even when the medical guidewire 1 itself is solely curved in the body, it is possible to reduce the sliding resistance between the second cylindrical part 11 and the cavity formed by passage of the coiled body 5.

A material for the coiled body 5 is not particularly limited. In the present embodiment, stainless steel (SUS304) is used as the material for the coiled body 5. Other than that, similarly to the core shaft 3, a material such as a super elastic alloy like an Ni—Ti alloy, a piano wire, or a tungsten wire may be used.

The coiled body 5 is wound in coiled shape around the tip portion of the core shaft 3. The coiled body 5 is fixed by brazing to the tip portion of the core shaft 3 in a plurality of places, including a coil-tip brazed portion 15 continued to the extreme tip portion 9, a plurality of coil-middle brazed portions that are located on the proximal end side of the coil-tip brazed portion 15 and include a coil-middle brazed portion 17, and a coil-base-end brazed portion 13 located at the proximal end of the coiled body 5.

It should be noted that in FIG. 1, only one coil-middle brazed portion 17 is illustrated, and the other coil-middle brazed portions are omitted.

In the vicinity of the extreme tip portion 9, the coiled body 5 is wound so as to generate a space between adjacent wires of the coiled body 5. On the other hand, on the proximal end side from the coil-middle brazed portion 17 that is adjacent to the proximal end side of the coil-tip brazed portion 15, the coiled body 5 is wound such that adjacent wires of the coiled body 5 are in contact with each other.

It is to be noted that diameters of the wires of the coiled body 5 in the present embodiment are uniform. However, the diameters of the wires of the coiled body 5 may be decreased gradually from the proximal end toward the tip of the coiled body 5. Further, the diameters of the wires of the coiled body 5 on the side closer to the tip than the coil-middle brazed portion 17 may be made smaller than those of the other wires of the coiled body 5.

Decreasing the diameters of the wires of the coiled body 5 gradually from the proximal end toward the tip of the coiled body 5 can gradually enhance the flexibility of the tip portion of the medical guidewire 1. This is effective in the case of curving the entire coiled body 5.

Meanwhile, making smaller the diameters of the wires of the coiled body 5, provided on the side closer to the tip than the coil-middle brazed portion 17, than those of the other wires of the coiled body 5 can enhance the flexibility of a portion on the side closer to the tip than the coil-middle brazed portion 17. This is effective in the case of curving the area on the side closer to the tip than the coil-middle brazed portion 17, with a relatively small radius of curvature.

Further, the outer surfaces of the medical guidewire 1 from the extreme tip portion 9 to the coiled body 5 and the second cylindrical part 11 are coated with a hydrophilic material 7.

Examples of the hydrophilic material may include a cellulose-based polymer, a polyethylene oxide-based polymer, a maleic anhydride-based polymer (e.g., maleic anhydride copolymer such as methyl vinyl ether-maleic anhydride copolymer), an acrylamide-based polymer (e.g., polyacrylamide, polyglycidyl methacrylate-dimethylacrylamide block copolymer), water-soluble nylon, polyvinyl alcohol, polyvinylpyrrolidone, and hyaluronate.

It is to be noted that the hydrophilic material 7 in the present embodiment is hyaluronate.

The hydrophilic material 7 coated on the medical guidewire 1 reduces the sliding resistance of the medical guidewire 1 inside the catheter, the tubular organ or the intracorporeal tissue.

By coating the second cylindrical part 11, with a smaller outer diameter than that of the coiled body 5, with the hydrophilic material 7 in the present embodiment, it is possible to significantly reduce the sliding resistance between the guiding catheter and the medical guidewire 1.

By applying the hydrophilic material 7 onto the outer surfaces of the medical guidewire 1 from the extreme tip portion 9 to the coiled body 5 and the second cylindrical part 11 such that the thickness is made uniform, it is possible to sufficiently reduce the sliding resistance.

It should be noted that the number of sliding of the medical guidewire 1 and the guiding catheter increases when a long period of time is required for the physician to perform the operation. In the present embodiment, consideration is also given in that respect.

Figure 2:
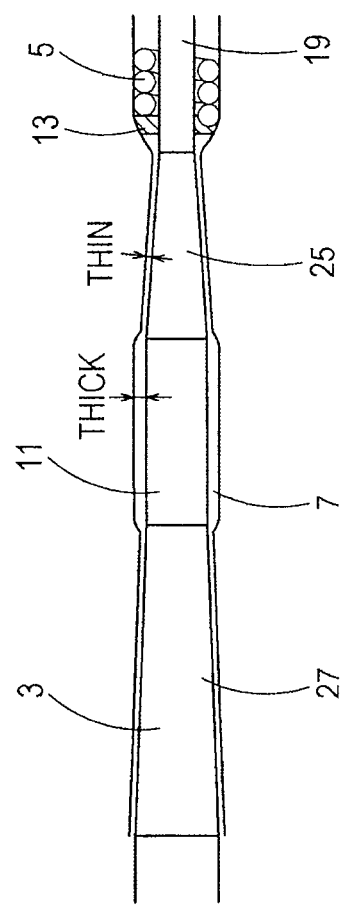
FIG. 2 illustrates a partially enlarged view of a second cylindrical part of a core shaft in the first embodiment.

FIG. 2 illustrates a partially enlarged view of the second cylindrical part of the core shaft in the present embodiment.

In FIG. 2, the hydrophilic material 7 coated on the second cylindrical part 11 is formed with a larger thickness than that of the hydrophilic material 7 coated on the coiled body 5.

That is, the hydrophilic material 7 is formed on the surface of the core shaft 3 such that a distance from the outer surface of the second cylindrical part 11 to the outer surface of the hydrophilic material 7 is longer than a distance from the outer surface of the coiled body 5 to the outer surface of the hydrophilic material 7.

Further, the hydrophilic material 7 coated on the second cylindrical part 11 is formed with a larger thickness than those of the hydrophilic materials 7 coated on the first taper part 27 and the second taper part 25 which are adjacent to the second cylindrical part 11.

Therefore, as illustrated in FIGS. 6 to 8, even when the medical guidewire 1 is slid for a long period of time with the guiding catheter curved, the sliding resistance in the second cylindrical part 11 does not increase.

Figure 2A:
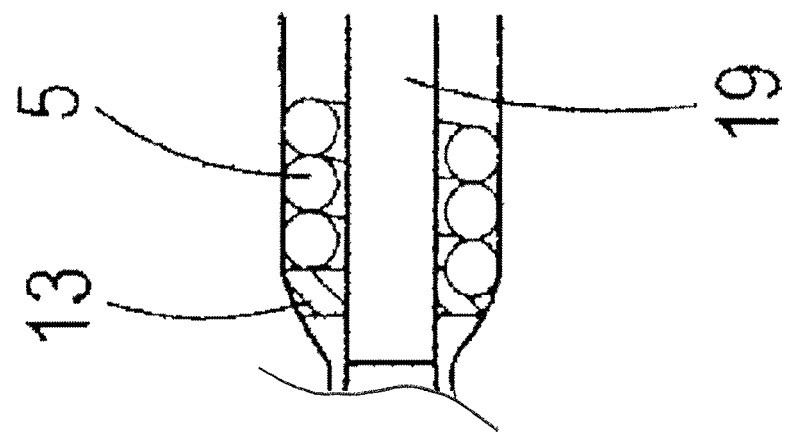
FIG. 2A illustrates a partially enlarged view of a cylindrical part including a coating of a hydrophilic material and a coiled body including the coating of the hydrophilic material in one embodiment.
Figure 2A:
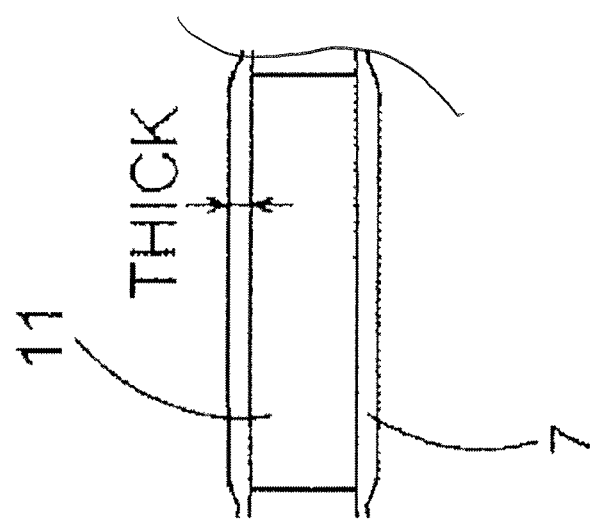

Further, as illustrated in FIG. 2A, the diameter of the second cylindrical part 11 including the hydrophilic material 7 is desirably smaller than that of the coiled body 5 including the hydrophilic material 7.

Making smaller the diameter of the second cylindrical part 11 including the hydrophilic material 7 than that of the coiled body 5 including the hydrophilic material 7 can generate a space between a cavity, formed by passage of the coiled body 5 through the inside of the guiding catheter, the tubular organ or the intracorporeal tissue, and the second cylindrical part located on the proximal end side of the coiled body 5. Thereby, even when the medical guidewire 1 is slid for a long period of time with the guiding catheter curved, the sliding resistance between the guiding catheter and the medical guidewire 1 can be kept low.

Meanwhile, it is also preferable to reduce the sliding resistance of the medical guidewire 1 not only in the case of pushing the medical guidewire 1 but also in the case of pulling the medical guidewire 1. In the present invention, consideration is also given in that respect.

Figure 3:
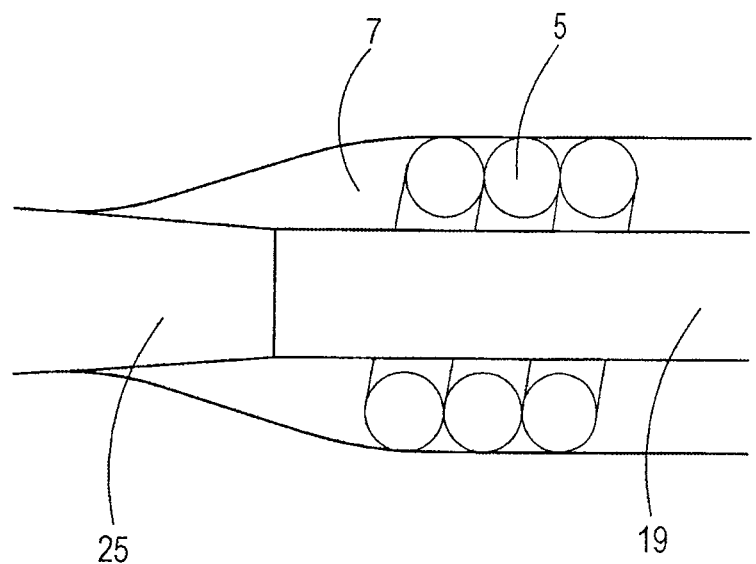
FIG. 3 illustrates a partially enlarged view of the state of connection between the core shaft and a coiled body in the first embodiment.

FIG. 3 illustrates a partially enlarged view of the state of connection between the core shaft and the coiled body in the present embodiment.

As illustrated in FIG. 3, the hydrophilic material 7 is applied so as to form a streamlined shape in the area from the proximal end portion of the coiled body 5 to the second taper part 25. It is thus possible to reduce the sliding resistance of the medical guidewire 1 at the time of pulling the medical guidewire 1 inside the guiding catheter, the tubular organ or the intracorporeal tissue.

In the present embodiment, the hydrophilic material 7 is applied so as to form the streamlined shape in the area from the proximal end portion of the coiled body 5 to the second taper part 25. However, this hydrophilic material 7 may be applied so as to form the streamlined shape in the area from the proximal end portion of the coiled body 5 to the second cylindrical part 11. It is thus possible to reduce a depressed portion of the second taper part 25. It is further possible to reduce the sliding resistance of the medical guidewire 1 at the time of pulling the medical guidewire 1 inside the guiding catheter, the tubular organ or the intracorporeal tissue.

It is to be noted that also in this case, the hydrophilic material 7 applied onto the second cylindrical part 11 is preferably formed with a larger thickness than those of the hydrophilic materials 7 applied onto the coiled body 5, the first taper part 27 and the second taper part 25.

In that case, it is possible to more favorably inhibit the increase in sliding resistance in the second cylindrical part 11 in the case of sliding the medical guidewire 1 for a long period of time with the guiding catheter curved.

Second Embodiment

Next, a second embodiment of the medical guidewire of the present invention will be described.

Figure 4:
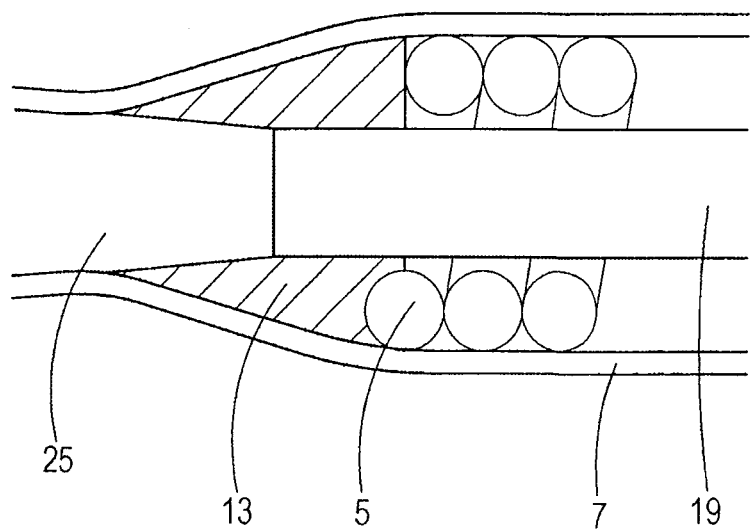
FIG. 4 illustrates a partially enlarged view of the state of connection between a core shaft and a coiled body in a second embodiment.

FIG. 4 illustrates a partially enlarged view of the state of connection between a core shaft and a coiled body in the second embodiment.

In FIG. 4, the coil-base-end brazed portion 13 is made of a brazing material in streamlined shape which is formed in the area from the proximal end portion of the coiled body 5 to the second taper part 25. The hydrophilic material 7 is applied with a uniform thickness onto the range from the coiled body 5 to the coil-base-end brazed portion 13 and the second taper part 25.

Also by means of this medical guidewire 1 of the second embodiment, it is possible to reduce the sliding resistance of the medical guidewire 1 at the time of pulling the medical guidewire 1 inside the guiding catheter, the tubular organ or the intracorporeal tissue.

In the second embodiment, in the area from the proximal end portion of the coiled body 5 to the second taper part 25, the brazed portion 13 is formed by use of the brazing material so as to form the streamlined shape. However, the area from the proximal end portion of the coiled body 5 to the second cylindrical part 11 may be formed in the streamlined shape by use of this brazing material. It is thus possible, as in the first embodiment, to reduce the depressed portion of the second taper part 25. It is further possible to reduce the sliding resistance of the medical guidewire 1 at the time of pulling the medical guidewire 1 inside the guiding catheter, the tubular organ or the intracorporeal tissue.

In this case, the hydrophilic material 7 is applied with a uniform thickness onto the area from the coiled body 5 to the coil-base-end brazed portion 13 and the second cylindrical part 11.

It is to be noted that also in this case, the hydrophilic material 7 applied onto the second cylindrical part 11 may be formed with a larger thickness than those of the hydrophilic materials 7 applied onto the coiled body 5, the first taper part 27 and the second taper part 25.

In that case, it is possible to more favorably inhibit the increase in sliding resistance in the second cylindrical part 11 in the case of sliding the medical guidewire 1 for a long period of time with the guiding catheter curved.

Third Embodiment

Next, a third embodiment of the medical guidewire of the present invention will be described.

Figure 5:
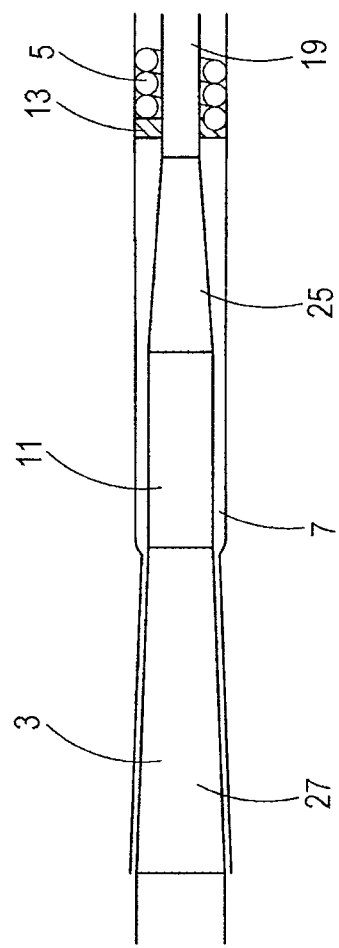
FIG. 5 illustrates a partially enlarged view of the state of connection between a core shaft and a coiled body in a third embodiment.

FIG. 5 illustrates a partially enlarged view of the state of connection between a core shaft and a coiled body in the third embodiment.

In the third embodiment, as illustrated in FIG. 5, the hydrophilic material 7 is applied so as to form a cylindrical shape (or linear shape) in a middle area from the proximal end portion of the coiled body 5 to the second cylindrical part 11. Further, the hydrophilic material 7 is applied so as to form a curved shape in a connecting section between this middle area and the proximal end portion of the coiled body 5, and applied so as to form a curved shape in a connecting section between the middle area and the second cylindrical part. It is thus possible to further reduce the sliding resistance of the medical guidewire 1 at the time of pulling the medical guidewire 1 inside the guiding catheter, the tubular organ or the intracorporeal tissue.

In an exemplary embodiment, there is a medical guidewire wherein a proximal end of the coiled body is joined to the core shaft at a joined portion, a first end of the joined portion closer to the proximal end of the coiled body has a first curved shape, a second end of the joined portion father from the proximal end of the coiled body has a second curved shape curved in a direction opposite the first curved shape, and the joined portion includes, from the first end to the second end, a streamlined shape in a longitudinal cross section of the guidewire. In yet another alternate embodiment, there is a medical guidewire wherein the proximal end of the coiled body is joined to the core shaft at a joined portion, a first end of the joined portion closer to the proximal end of the coiled body has a first curved shape, a second end of the joined portion father from the proximal end of the coiled body has a second curved shape curved in a direction opposite the first curved shape, and the joined portion includes, from the first end to the second end, a streamlined shape in a longitudinal cross section of the guidewire.

While the invention has been shown and described in detail, the foregoing description is in all aspects illustrative and not restrictive. It is therefore understood that numerous modifications and variations can be devised without departing from the spirit and scope of the invention.

REFERENCE SIGNS LIST 1 medical guidewire
3 core shaft
5 coiled body
7 hydrophilic material
9 extreme tip portion
11 second cylindrical part
13 coil-base-end brazed portion
15 coil-tip brazed portion
17 coil-middle brazed portion
19 third cylindrical part
21 first cylindrical part
25 second taper part
27 first taper part
29 third taper part
31 fourth cylindrical part
33 taper press part
35 cylindrical press part
53 aortic valve
55 aortic arc
57 descending aorta
59 right coronary artery
61 left main trunk
63 left anterior descending artery
65 ascending aorta
67 left coronary artery
69 left circumflex artery
71 stenosis part

The invention claimed is:

1. A medical guidewire, comprising:
a core shaft;
a coiled body that covers at least a distal end of the core shaft, wherein the core shaft has a cylindrical part, with a smaller diameter than that of the coiled body, on a side of a proximal end of the coiled body; and
a coating of a hydrophilic material on an outer surface of the cylindrical part and on an outer surface of the coiled body,
wherein a thickness of the coating on the cylindrical part is larger than on the coiled body, and
wherein an outer diameter of the coating onto the cylindrical part is smaller than onto the coiled body.

2. The medical guidewire according to claim 1, wherein a diameter of the cylindrical part including the hydrophilic material is smaller than that of the coiled body including the hydrophilic material.

3. The medical guidewire according to claim 2, wherein
the proximal end of the coiled body is joined to the core shaft at a joined portion,
a first end of the joined portion closer to the proximal end of the coiled body has a first curved shape,
a second end of the joined portion father from the proximal end of the coiled body has a second curved shape curved in a direction opposite the first curved shape, and the joined portion includes, from the first end to the second end, a streamlined shape in a longitudinal cross section of the guidewire.

4. The medical guidewire according to claim 1, wherein the proximal end of the coiled body is joined to the core shaft at a joined portion,
a first end of the joined portion closer to the proximal end of the coiled body has a first curved shape,
a second end of the joined portion father from the proximal end of the coiled body has a second curved shape curved in a direction opposite the first curved shape, and
the joined portion includes, from the first end to the second end, a streamlined shape in a longitudinal cross section of the guidewire.

5. A medical guidewire, comprising:
a core shaft;
a coiled body that covers at least a distal end of the core shaft, wherein the core shaft has a cylindrical part, with a smaller diameter than that of the coiled body, on a side of a proximal end of the coiled body; and
a coating of a hydrophilic material on an outer surface of the cylindrical part and on an outer surface of the coiled body,
wherein a thickness of the coating on the cylindrical part is larger than on the coiled body, and
wherein an outer diameter of the cylindrical part, including the coating thereon, is less than an outer diameter of the coiled body, including the coating thereon.

6. The medical guidewire according to claim 5, wherein:
a diameter of the cylindrical part including the hydrophilic material is smaller than that of the coiled body including the hydrophilic material.

7. The medical guidewire according to claim 6, wherein:
the proximal end of the coiled body is joined to the core shaft at a joined portion,
a first end of the joined portion closer to the proximal end of the coiled body has a first curved shape,
a second end of the joined portion father from the proximal end of the coiled body has a second curved shape curved in a direction opposite the first curved shape, and
the joined portion includes, from the first end to the second end, a streamlined shape in a longitudinal cross section of the guidewire.

8. The medical guidewire according to claim 5, wherein:
the proximal end of the coiled body is joined to the core shaft at a joined portion,
a first end of the joined portion closer to the proximal end of the coiled body has a first curved shape,
a second end of the joined portion father from the proximal end of the coiled body has a second curved shape curved in a direction opposite the first curved shape, and
the joined portion includes, from the first end to the second end, a streamlined shape in a longitudinal cross section of the guidewire.

9. The medical guidewire according to claim 5, wherein:
an outer profile of the coating of the hydrophilic material, extending in a longitudinal direction of the guidewire from at least about the coiled body to a location proximal the coiled body, is streamlined.

10. The medical guidewire according to claim 5, wherein:
an outer profile of the coating of the hydrophilic material, extending in a longitudinal direction of the guidewire from at least about the coiled body to a location proximal the coiled body, includes a surface with at least two curves, wherein one of the curves is convex relative to the core shaft and another of which is concave relative to the core shaft.

11. The medical guidewire according to claim 5, wherein:
an outer profile of the coating of the hydrophilic material, extending in a longitudinal direction of the guidewire from at least about the coiled body to a location proximal the coiled body, includes a surface having tangent lines that gradually change along the longitudinal direction.

12. The medical guidewire according to claim 5, wherein:
an outer profile of the coating of the hydrophilic material, extending in a longitudinal direction of the guidewire from at least about the coiled body to a location proximal the coiled body, includes a surface that includes:
a component that is parallel to the longitudinal direction in the area proximate the coiled body;
a component that extends from the parallel component that is concave relative to the core shaft; and
a component that is convex relative to the core shaft, the convex component being proximate, relative to the coiled body, to the concave component.

13. The medical guidewire according to claim 12, wherein:
the surface includes a component that extends at an oblique angle relative to the longitudinal direction of the guidewire, and wherein the oblique angle component extends from the concave component to the convex component.

14. The medical guidewire according to claim 13, wherein:
the surface includes a component that extends at a second oblique angle relative to the longitudinal direction of the guidewire, and wherein the second oblique angle component extends from the convex component in a direction proximal from the coiled body, wherein the first oblique angle is an acute oblique angle when measured from the longitudinal direction and opening towards the core shaft, and wherein the second oblique angle is an obtuse angle when measured from the longitudinal direction and opening towards the core shaft.

15. The medical guidewire according to claim 12, wherein:
the surface includes a component that extends at an oblique angle relative to the longitudinal direction of the guidewire, and wherein the oblique angle component extends from the convex component in a direction proximal from the coiled body.

16. The medical guidewire according to claim 15, wherein:
the oblique angle component extends from the convex component to a location at least substantially proximate the cylindrical part.

17. A medical guidewire, comprising:
a first section at a distal location along the guidewire, the first section including a coiled body coated with a hydrophilic material, the maximum outer diameter of the first section being a first value;
a second section proximal the first section, the second section including a cylindrical section of a core shaft coated with a hydrophilic material, the maximum outer diameter of the second section being a second value;
a third section contiguous with the first section having a series of maximum outer diameters decreasing in value from the first value with respect to location along the longitudinal axis in the proximal direction from the distal end of the guidewire; and
a fourth section contiguous with the third section having a series of maximum outer diameters increasing in value from a smallest value of the third section with respect to location along the longitudinal axis in the proximal direction from the distal end of the guidewire, wherein the fourth section is in between the second section and the third section,
wherein the first value is greater than the second value, and wherein all diameters lie on a plane normal to a longitudinal axis of the guidewire.

18. The medical guidewire of claim 17, wherein the first section has a series of maximum outer diameters that are the same with respect to location along the longitudinal axis from in the proximal direction away from a distal end of the guidewire, and wherein the second section has a series of maximum outer diameters that are the same with respect to location along the longitudinal axis in the proximal direction away from a distal end of the guidewire.

19. The medical guidewire of claim 17, wherein the first section has a series of maximum outer diameters that are the same with respect to location along the longitudinal axis along a distance of at least 10 mm from in the proximal direction away from a distal end of the guidewire, and wherein the second section has a series of maximum outer diameters that are the same with respect to location along the longitudinal axis along a distance of at least 10 mm in the proximal direction away from a distal end of the guidewire.

\* \* \* \* \*